United States Patent [19]

Arndt et al.

[11] Patent Number: 4,614,827
[45] Date of Patent: Sep. 30, 1986

[54] METHOD FOR ISOLATING VINYL SALT COMPOUNDS FROM AQUEOUS SOLUTIONS

[75] Inventors: Peter J. Arndt, Seeheim-Jugenheim; Franz Wenzel, Darmstadt; Manfred Müller, Rossdorf; Fritz Schlosser, Darmstadt, all of Fed. Rep. of Germany

[73] Assignee: Röhm GmbH, Darmstadt, Fed. Rep. of Germany

[21] Appl. No.: 629,358

[22] Filed: Jul. 10, 1984

[30] Foreign Application Priority Data

Jul. 20, 1983 [DE] Fed. Rep. of Germany ....... 3326117
May 19, 1984 [DE] Fed. Rep. of Germany ....... 3418664

[51] Int. Cl.$^4$ .............................................. C07F 3/06
[52] U.S. Cl. .................................. 556/131; 556/55; 556/114; 556/105; 556/44; 556/77; 556/49; 560/222; 562/598; 562/600; 564/204
[58] Field of Search ............... 560/222; 562/598, 600; 564/204; 260/429.9; 556/131, 44, 49, 105, 77, 114, 55

[56] References Cited

U.S. PATENT DOCUMENTS

| | | | |
|---|---|---|---|
| 2,103,265 | 12/1937 | Lott | 560/222 |
| 2,395,307 | 2/1946 | Weber et al. | 260/429.9 X |
| 2,677,699 | 5/1954 | Barney | 260/486 |
| 2,741,568 | 4/1956 | Hayek | 117/139.5 |
| 2,980,657 | 4/1961 | Melamed | 260/86.1 |
| 3,021,364 | 2/1962 | Cornell et al. | 260/429.9 X |
| 3,024,222 | 3/1962 | Freedman et al. | 260/429.9 X |
| 3,227,738 | 1/1966 | Klemchuk | 260/429.9 X |
| 3,285,945 | 11/1966 | Wember | 260/429.9 |
| 3,291,818 | 12/1966 | Ratz et al. | 260/435 |
| 3,336,358 | 8/1967 | McFadden | 560/222 |
| 3,420,932 | 1/1969 | Jones et al. | 260/448 AD |
| 3,493,550 | 2/1970 | Schmitt et al. | 260/86.1 |
| 3,689,427 | 9/1972 | Matsuda | 260/429.9 X |
| 3,714,136 | 1/1973 | Gershberg | 260/89.75 |
| 3,803,189 | 4/1974 | Haglid | 260/429.9 X |
| 3,916,015 | 10/1975 | Yates | 260/429.9 X |
| 4,055,581 | 10/1977 | Hopkins et al. | 260/429.9 |
| 4,060,535 | 11/1977 | Cinco | 562/598 X |
| 4,100,182 | 7/1978 | Martin et al. | 260/429.9 |
| 4,180,681 | 12/1979 | Leonard et al. | 562/598 X |
| 4,187,353 | 2/1980 | Schroeder | 521/149 |
| 4,214,000 | 7/1980 | Papa | 260/429.9 X |
| 4,239,876 | 12/1980 | Arndt et al. | 526/287 |
| 4,500,466 | 2/1985 | Hayes et al. | 260/429.9 |

FOREIGN PATENT DOCUMENTS

| | | |
|---|---|---|
| 1156000 | 10/1983 | Canada . |
| 1443694 | 3/1969 | Fed. Rep. of Germany . |
| 2009748 | 9/1971 | Fed. Rep. of Germany . |
| 3011306 | 10/1980 | Fed. Rep. of Germany . |
| 3202663 | 8/1983 | Fed. Rep. of Germany . |
| 3224927 | 1/1984 | Fed. Rep. of Germany . |
| 3224928 | 1/1984 | Fed. Rep. of Germany . |
| 1332247 | 10/1973 | United Kingdom . |
| 1353212 | 5/1974 | United Kingdom . |
| 2046748 | 11/1980 | United Kingdom . |
| 2096624 | 10/1982 | United Kingdom . |

OTHER PUBLICATIONS

Chemical Abstracts, 87, 5403q (1977).
Chemical Abstracts, 66, 56358c (1967).
Hackh's Chemical Dictionary, McGraw-Hill Book Co., 3rd Edition, pp. 288 and 799 (1944).

*Primary Examiner*—Helen M. S. Sneed
*Attorney, Agent, or Firm*—Curtis, Morris & Safford

[57] ABSTRACT

A method for isolating a vinyl salt compound in solid form from an aqueous solution thereof by spray drying such an aqueous salt solution.

12 Claims, No Drawings

METHOD FOR ISOLATING VINYL SALT COMPOUNDS FROM AQUEOUS SOLUTIONS

The present invention relates to a method for isolating vinyl salt compounds, particularly polymerizable compounds of this type, in solid form from aqueous solution.

Various types of vinyl salt compounds are used in industry, mainly as monomers in the production of polymers or copolymers. Quaternary ammonium groups, for example, are widely incorporated into molecules intended to be water soluble.

Vinylic quaternary ammonium compounds, and especially those derived from vinylcarboxylic acids such as acrylic or methacrylic acid, which are capable of free radical polymerization, are of particular interest. [See W. F. Hoover in Macromol. Sci. Chem, A4 (6), pp. 1327-1417, (1970).] The uses for the cationic quaternary polyelectrolytes produced therefrom range from flocculants, sedimentation aids, and thickeners to hairspray additives. (See Hoover, loc. cit.)

The anion associated with monomeric quaternary ammonium salts is usually supplied by the quaternization reagent. The use of quaternary ammonium derivatives of acrylic or methacrylic acid obtained by means of a dialkyl sulfate, and particularly of dimethyl sulfate, predominates. The quaternization of dimethylaminoethyl methacrylate with dimethyl sulfate is described in U.S. Pat. No. 2,677,699, for example. The quaternization of an aqueous solution containing more than 50 percent of diethylaminoethyl acrylate with dimethyl sulfate at 30° to 35° C. is described also in U.S. Pat. No. 2,741,568. However, the halides of this class of compounds have also been used in the preparation of polymers. [See G. C. Overberger et al. in J. Polym. Science XXVII, pp. 381-390 (1958).]

The polymerization of such monomers clearly proceeds better in aqueous solution than in other solvents since transfer reactions, which have an adverse effect on the polymer, are then rarer. It is known from published German patent application DOS No. 20 09 748, that the polymerization can be expected to proceed particularly well when concentrated aqueous solutions of the monomers are used.

By the use of highly concentrated aqueous solutions, it is possible to some extent to avoid the difficulties which the concentration of more dilute solutions entails. Even isolation, from an aqueous solution, of the polymers formed from quaternary ammonium salts is onerous in practice as it must be done by removal of the water by azeotropic distillation or by the use of drying rolls. (See U.S. Pat. No. 3,714,136.)

Directly polymerizable mixtures of acrylamide and quaternization products of tertiary aminoalkyl esters or tertiary aminoalkylamides of acrylic or methacrylic acid can be obtained in the absence of water, that is to say, without the use of solvents, according to German Pat. No. 2,848,627 (=U.S. Pat. No. 4,239,876). In U.S. Pat. No. 2,980,657, quaternization is effected in the presence of absolute ethanol as solvent; and in Japanese patent publication 77-148018, saturated or unsaturated aliphatic nitriles are used as solvents.

In addition to quaternary ammonium salts derived from amine substituted esters or amides of acrylic acid and of methacrylic acid, metal and ammonium salts of vinylcarboxylic acids such as acrylic acid and methacrylic acid are used in industry.

In German Pat. No. 27 26 260 (=U.S. Pat. No. 4,187,353), for example, a foamable polymeric material is described which contains a metal salt of acrylic acid or of methacrylic acid as the monomer. The $Mg^{2+}$, $Zr^{4+}$, $Cr^{3+}$, $Co^{2+}$, $Zn^{2+}$, $Cd^{2+}$, $Bi^{3+}$, $TiO^{2+}$ and $Pb^{2+}$ salts of acrylic acid and/or of methacrylic acid are named.

Ionically crosslinked acrylic resins produced by free radical polymerization of a monomer mixture of at least 50 weight percent of acrylic acid esters or of methacrylic acid esters and from 0.1 to 50 weight percent of at least one salt of acrylic acid and/or of methacrylic acid with a metal cation of an element from the group consisting of zinc, aluminum, tin, lead, titanium, zirconium, and hafnium are described in published German patent application DOS No. 29 43 566. U.S. Pat. No. 3,493,550 relates to ionically crosslinked copolymers of methyl methacrylate and metal salts of methacrylic acid. In published German patent application DOS No. 29 43 566, it is pointed out that in most cases the metal salts of acrylic and methacrylic acid are difficult to isolate.

As a rule, the tendency of the acids and salts to polymerize is a limiting factor in their production and isolation. The starting materials are usually free acids which are conventionally reacted with appropriate basic compounds of the metals. When the reaction medium is water, the salts are often obtained only after concentration by evaporation and usually contain water. It has been sought to circumvent the isolation of metal salts having a pronounced tendency to polymerize by using the unsaturated acids together with basic metal compounds in the polymerization recipe. (Published German patent application DOS No. 31 14 266.) For example, published German patent application DOS No. 32 24 298 describes a process for the preparation of metal salts of methacrylic acid or of acrylic acid by reaction of the acids with the oxides or hydroxides of the metals of main and subgroups I, II, and IV, and of subgroup VIII having an oxidation number not greater than two, wherein the metal oxides or hydroxides are reacted, without the addition of a solvent, with at least 1.5 times the stoichiometrically required amount of methacrylic acid or of acrylic acid. The reaction of metal carbonates with acrylic or methacrylic acid in excess without the use of solvents is also possible. (Published German patent application DOS No. 32 24 927.)

The preparation of the ammonium salts of acrylic acid or of methacrylic acid by the reaction of the acids in an aqueous medium with gaseous ammonia is described in published German patent application DOS No. 32 02 663, which points out that the temperature during the reaction and the subsequent working up should not be appreciably above room temperature.

It has generally been sought in the prior art to overcome the difficulties in recovering such salts, which difficulties arise mainly from the pronounced tendency toward polymerization or other reactivity of vinyl salt compounds activated in the alpha position, by adjusting the parameters of the reaction for minimal tendency toward polymerization, allowance being made for the fact that the purity and homogeneity of the product must meet minimum requirements. This means, for example, that the process must be carried out at a temperature not higher than room temperature if the salts are to be isolated from from an aqueous solution. Past experience has shown that the removal of the water by azeotropic distillation with the aid of inert organic solvents will not sufficiently reduce the risk of polymerization.

Moreover, a number of proposals have, in effect, tended to make the manufacturing process more time consuming, costly, and complicated than seems reasonable in view of the simple reactions involved.

Thus, there has been a continuing need for a process that would make it possible to prepare and isolate vinyl salt compounds meeting minimum purity and homogeneity requirements, particularly the salts and salt-like derivatives of vinylcarboxylic acids, from aqueous solutions in a simpler manner and in less time and at lower cost then heretofore.

To accomplish this object, a method for the isolation of vinyl salt compounds in solid form from aqueous solutions thereof is proposed wherein aqueous solutions of the vinyl salt compounds are subjected to spray drying. (As usual, for vinyl compounds to be present in salt form, they must be capable of dissociating in aqueous solution into cations different from hydrogen and into anions. The presence of betaines is also possible.)

Vinyl salt compounds within the meaning of the present invention are primarily the compounds used industrially, mainly as monomers in polymerization reactions. The present process is directed in particular to the isolation of salts of vinylcarboxylic acids, and more particularly of acrylic acid and of methacrylic acid, maleic acid, fumaric acid, and itaconic acid. The method of the invention thus is suitable primarily for use with the industrially utilizable salts of vinylcarboxylic acids, for example those named in the prior art. (See W. F. Hoover, loc. cit., and the patent publications.) In the practice of the process of the invention, the salts are present in aqueous solution, and possibly also in a mixture of water and an organic water miscible solvent such as an alcohol, acetone, and the like.

The use of the method of the invention is indicated particularly when the vinyl salt compounds possess sufficient water solubility. Sufficient water solubility here means a solubility of at least 28 g of the salt in 100 g of water at room temperature (20° C.). Of special interest are the salts of acrylic and methacrylic acid and also of maleic acid, fumaric acid, and itaconic acid, and more particularly the alkali metal salts, and especially the sodium, potassium, and lithium salts; the alkaline earth metal salts, and especially the magnesium, calcium, strontium, and barium salts; the salts of subgroups I and II of the periodic table, and especially the copper and zinc salts; the salts of main and subgroup IV (Ge, Sn, Pb, Ti, Zr, Hf), and especially the germanium, tin, lead, titanium, and zirconium salts; the salts of subgroup VIII (Fe, Ru, Os, Co, Rh, Ir, Ni, Pd, Pt), and especially the iron, cobalt, and nickel salts; the salts of main and subgroups V ((As, Sb, Bi, V, Nb, Ta) and of subgroup VII (Mn, Tc, Re), and especially the antimony, bismuth, vanadium, and manganese salts; and the ammonium salts, including those derived from ammonium cations of the formula

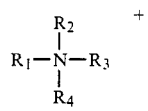

wherein $R_1$ and $R_2$ are hydrogen or an alkyl group having from 1 to 18 carbon atoms, and preferably from 1 to 5 carbon atoms, and $R_3$ and $R_4$ are hydrogen or an alkyl group having from 1 to 18 carbon atoms, and preferably from 1 to 6 carbon atoms, or wherein $R_3$ and $R_4$, optionally with inclusion of one or two further hetero atoms such as nitrogen, oxygen, or sulfur, form a five- or six-membered heterocyclic system.

Particularly well suited for use are:

|  | Water solubility at 20° C. in g/salt/100 g water |
|---|---|
| Potassium methacrylate | 101.8 |
| Sodium methacrylate | 95.3 |
| Lithium methacrylate | 87.5 |
| Ammonium methacrylate | 104.5 |
| Strontium dimethacrylate | 27.5 |
| Barium dimethacrylate | 40.5 |
| Sodium acrylate | 49.0 |
| Potassium acrylate | 166.5 |
| Ammonium acrylate | 242.0 |
| Strontium diacrylate | 68.0 |
| Calcium diacrylate | 35.0 |
| Lithium acrylate | 45.0 |
| Barium diacrylate | 74.0 |
| Zinc diacrylate | 40.0 |

Preferred vinyl salt compounds are, moreover, the quaternary ammonium salts of the formula

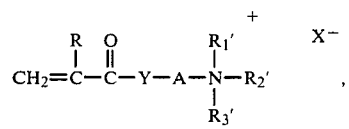

wherein R is hydrogen or methyl; Y is oxygen or $-NR_4$, $R_4$ being hydrogen or an alkyl group having from 1 to 6 carbon atoms; A is an optionally branched hydrocarbon bridge having from 2 to 8 carbon atoms; $R_1'$ and $R_2'$ are, independently of each other, alkyl groups having from 1 to 6 carbon atoms or benzyl; $R_3'$ is an alkyl group having from 1 to 6 carbon atoms, or a $-CH_2-CH=CH_2$, $-CH_2-O-CH_3$, or $-CH_2-CH_2-OH$ group; and X is the anion from the quaternizing reagent.

The process of the invention is applicable in principle to aqueous solutions of quaternary ammonium salts of vinyl compounds without distinction. In addition to the compounds of the aforementioned formula, these include quaternary diallyl- and allyl-ammonium salts, vinyloxyalkylammonium salts, vinylbenzylammonium and vinylanilinium salts, etc.

Esters and amides of the aforementioned formula wherein R is methyl, that is, quaternary ammonium salt derivatives of methacrylic acid, as well as those of acrylic acid, are particularly suitable. Moreover, compounds of the formula wherein A is a $-(CH_2)_2-$, $-(CH_2)_3-$, or $-CH_2-C(CH_3)_2-CH_2-$ group are preferred. Of special interest are also compounds wherein $R_1'$, $R_2'$, and $R_3'$ are methyl or ethyl. From an industrial point of view, important anions are particularly the chloride and also the dimethyl sulfate. Examples are trimethylammoniumethyl methacrylate chloride and the corresponding triethylammonium compound.

The concentration of the solid product in the aqueous solution is not critical to the method of the invention over a wide range. In view of the method of preparation of the quaternary ammonium salts, however, highly concentrated solutions on the order of 50 to 85% solid product in the aqueous solution are desirable.

In the interest of a favorable energy balance, fairly concentrated salt solutions should be used in every case in the process of the invention. While lower salt contents usually will not be a limiting factor from the technical point of view, they will make the process less economical.

As a rule, the salt content of the solutions to be used in accordance with the invention will range from 20 weight percent to saturation concentration. For acrylates, for example, 35 weight percent will serve as a guide. The aqueous salt solutions of vinylcarboxylic acids, for example, may be prepared conventionally, for example, by neutralization of the acids with oxides, hydroxides, alkoxides, carbonates or bicarbonates of the metals or ammonium compounds whose salts are to be isolated, or optionally also with salts of other, volatile and, in particular, weak acids. The preparation of the salts in an aqueous medium is advantageously carried out so that the aqueous solutions formed can be directly processed in accordance with the invention by spray drying. Here and in carrying out the process of the invention, it is advisable to add commonly used stabilizers or polymerization inhibitors such as quinones, phenols, methylene blue, aromatic amines (e.g., diphenylamine), or nitro compounds, and optionally also copper or iron salts, in the amounts commonly used. Examples are the monomethyl ether of hydroquinone and 4-methyl-2,6-di-tert-butylphenol. (See Houben-Weyl, 4th ed., vol. XIV/1, pp. 42 and 1011, Georg Thieme Verlag, 1961.) The amounts to be added will usually range from 0.01 to 0.1 weight percent, based on the monomeric vinyl compounds to be stabilized.

For the sake of obtaining a product of maximum homogeneity, the use of excesses of reactants, for example, will be dispensed with in the preparation of the salts. For example, approximately stoichiometric amounts of the base contributing the cation will be used in neutralization. Aqueous solutions of salts of vinylcarboxylic acids obtained in some other way may, of course, also be used in the process of the invention.

In line with the usual terminology, spray drying here means the dispersing of liquid materials into fine, mist-like droplets and the drying thereof, usually with a hot air stream. (See Ullmanns Enzyklopädie der technischen Chemie, 4th ed., vol. 2, pp. 712–713, Verlag Chemie, 1972.) Nozzles (one- or two-fluid) or rotating disks with a speed ranging from 4,000 to 30,000 rpm are used as atomizing devices. (See Masters, Ind. Eng. Chemistry 60 [1968], No. 10, pp. 53–63.) The air inlet temperature advantageously ranges from 100° to 200° C., and the outlet temperature from 50° to 100° C., preferably from 90° to 100° C. The retention time in the dryer ranges from about 0.1 to 30 sec, advantageously from 0.5 to 10 sec.

The process of the invention will now be described in greater detail.

To prepare a salt solution, the desired amount of water is charged to a suitable stirrable and coolable vessel together with the $\alpha,\beta$-unsaturated carboxylic acid and the stabilizer and the basic metal compound is then added in portions while air is being fed in. Provision should be made for preventing the temperature from rising above 30° C., by cooling if desired. When all of the material has gone into solution, the solution is filtered with an appropriate filter. As a rule, a clear solution having the predetermined salt content will be obtained.

Spray drying of the vinyl salt compounds may be carried out with prior art spray drying equipment. For example, disk atomizer spray drying towers operating at speeds ranging from 4,000 to 30,000 rpm, and preferably from 22,000±5,000 rpm, may be used to advantage. The use of closed disks, for example, is advantageous. In many cases, it will be advisable to seek to secure the finest atomization of the material possible by operating in the upper rotation speed range. The air inlet temperature should range from 100° to 200° C. and is preferably 192°±5° C., while the outlet temperature should range from 50° to 100° C. and is preferably 90°±5° C. The retention time should be between 0.1 and 30 seconds, preferably is between 0.5 and 10 seconds, and more particularly is 7±2 seconds. A guide for the drying air feed rate is 400 to 20,000 m$^3$/hr. A hose pump may be used as a metering device. Screening may be done by means of a suitable screen such as an 0.8 mm Allgaier type screen.

A better understanding of the invention and of its many advantages will be had by referring to the following specific Examples, given by way of illustration.

EXAMPLE 1

About 20 kg of an approximately 35% zinc diacrylate solution were spray dried in a disk atomizer spray drying tower equipped with a standard disk rotating at 20,000 rpm, the air inlet temperature being 190° C., and the air outlet temperature being between 91° and 95° C. The drying air feed rate was about 400 m$^3$/hr. The retention time ranged from 5 to 10 sec. The throughput was 21.07 kg of zinc diacrylate solution (35%) per hour. The spray drying yield was better than 84 percent.

Clear beads, some of them vitrified, were obtained. The major portion of these ranged in size from 10 to 20 microns; the largest particles were about 80 microns. The residual moisture of the spray dried material ranged from 0.35 to 0.55 percent and the bulk density from 540 to 600 grams/liter. Higher bulk densities can be obtained by increasing the operating temperature. Because of the good water solubility of the products being dried, the spray drying apparatus can be cleaned quite easily.

Polymerization to a measurable degree was not observed. Salts of the metals of main and subgroups I, II, IV, V and VII and of subgroup VIII can be similarly isolated, especially the K$^+$, Na$^+$, Li$^+$, Sr$^{2+}$, and Sn$^{2+}$ salts, and also ammonium salts.

EXAMPLE 2

This example relates to the use of the process with quaternary ammonium salts.

Starting with dimethylaminoethyl methacrylate, methyl chloride, water and stabilizer, an aqueous trimethylammonium ethyl methacrylate chloride solution with a solids content of approximately 80% was obtained by pressure quaternization, which solution was then spray dried. Spray drying was carried out in a disk atomizer spray drying tower (NIRO, Minor-Production model) with maximum water evaporation of about 30 kg of water per hour, an air throughput of about 400 m$^3$/hr, an air inlet temperature of about 250° C., and a variable disk speed of up to about 20,000 rpm. At hot air inlet temperatures of 125°±25° C., trimethylammonium ethyl methacrylate chloride solution was fed at the rate of 20 kg/hr to the apertured disk rotating at about 15,000 rpm. The exit air temperature was 80°±10° C. Trimethylammonium ethyl methacrylate chloride with a residual moisture content of less than 1% was discharged from the cyclone following the spray dryer at the rate of about 15 kg/hr, representing a yield of approximately 95%. The spray dried product was free of polymers and proved highly suitable for the production of high molecular weight polymers to be used as flocculants. Thus, polymerization in a 75% aqueous solution yielded a high molecular weight product which, at a concentration of 1% in water, was found to have a viscosity of 7,000 mPa.sec and exhibited outstanding flocculating properties. In an analogous fashion, other quaternary ammonium salts of the formula given above can be produced, e.g. trimethylammonium propyl acrylate chloride or methosulfate or methacrylate chloride or methosulfate, 2-benzyldimethylammonium ethyl acrylate chloride or the corresponding methacrylic ester.

EXAMPLE 3

About 40 kg of an approximately 45% aqueous sodium methacrylate solution are spray dried in a disk atomizer spray drying tower equipped with a standard disk rotating at 20,000 rpm, the air inlet temperature being 185° C. and the outlet temperature being between 85° and 90° C. The drying air feed rate is about 400 m³/hr. The retention time ranges from 7 to 12 sec. The throughput is 23.7 kg of sodium methacrylate solution (45%) per hour. The spray drying yield is 10.3 kg solid material per hour, corresponding to 96.6% yield.

Clear beads in the range of 10 to 100 microns are obtained. The residual moisture of the spray dried material is less than 0.3%. The product is readily water soluble and is essentially free of polymer.

Other salts of methacrylic acid can be isolated in an analogous fashion. e.g. salts of the metals of main and subgroups I, II, IV, V and VII and of subgroup VIII.

EXAMPLE 4

The disodium salt of itaconic acid in a 40% aqueous solution was produced by reaction of itaconic acid in water with 2 mols of sodium hydroxide. The product thus formed is filtered to yield a perfectly clear solution.

The solution is spray dried under conditions essentially identical with the ones given in Example 3. The throughput is 23.3 kg of disodium salt of itaconic acid (40 % melting point 290° to 300° C.). One obtains 8.3 kg of solid material per hour corresponding to 89% yield. In a similar fashion other salts of vinylcarboxylic acids, e.g. the potassium or the ammonium salt, can be produced.

What is claimed is:

1. A method for isolating a monomeric salt of a polymerizable vinylcarboxylic acid or of a quaternized amide of a polymerizable vinylcarboxylic acid in solid form from an aqueous solution thereof, which comprises spray drying such an aqueous salt solution.

2. A method as in claim 1 wherein the air inlet temperature employed in said spray drying ranges from 100° to 200° C. and wherein the exit temperature employed in said spray drying ranges from 20° to 100° C.

3. A method as in claim 1 wherein said vinylcarboxylic acid is acrylic acid, methacrylic acid, maleic acid, fumaric acid, or itaconic acid.

4. A method as in claim 1 wherein said vinyl salt compound is a salt of a metal of main or subgroups I, II, IV, V, or VII, or of subgroup VIII of the periodic table, or is an ammonium salt.

5. A method as in claim 1 wherein said salt is an alkali metal, alkaline earth metal, or ammonium salt.

6. A method as in claim 1 wherein said salt is a zinc salt.

7. A method as in claim 1 wherein said vinyl salt compound is a quaternary ammonium salt of the formula

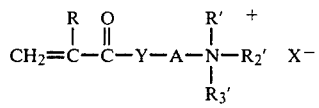

wherein

R is hydrogen or methyl;

Y is oxygen or $-NR_4$, $R_4$ being hydrogen or alkyl having from 1 to 6 carbon atoms;

A is linear or branched hydrocarbon having from 2 to 8 carbon atoms;

$R_1'$ and $R_2'$ are the same or different alkyl having from 1 to 6 carbon atoms or benzyl;

$R_3'$ is alkyl having from 1 to 6 carbon atoms, $-CH_2-CH=CH_2$, $-CH_2-O-CH_3$, or $-CH_2-CH_2-OH$; and X is the anion of the quaternizing reagent.

8. A method as in claim 7, wherein $X^-$ is a chloride, bromide, iodide, methyl sulfate, or tosylate.

9. A method as in claim 1 wherein the water solubility of said vinyl salt compound is at least 20 g in 100 g of water at 20° C.

10. A method as in claim 1 wherein said aqueous solution contains at least 20 weight percent of salt.

11. A method as in claim 1 wherein the air inlet temperature employed in said spray drying ranges from 100° to 200° C.

12. A method as in claim 1 wherein the exit temperature employed in said spray drying ranges from 50° to 100° C.

* * * * *